United States Patent [19]
Cheng et al.

[11] 3,987,040
[45] Oct. 19, 1976

[54] 3-SUBSTITUTED METHYL-7-ACYLAMINO-7-METHOXY-2-CEPHEM-4-CARBOXYLIC ACID AND ITS ESTERS

[75] Inventors: Theresa Y. Cheng, Newark; Sandor Karady, Elizabeth; Seemon H. Pines, Murray Hill; Meyer Sletzinger, North Plainfield, all of N.J.

[73] Assignee: Merck & Co., Inc., Rahway, N.J.

[22] Filed: Dec. 5, 1974

[21] Appl. No.: 529,863

Related U.S. Application Data

[60] Division of Ser. No. 201,210, Nov. 22, 1971, abandoned, which is a continuation-in-part of Ser. Nos. 162,703, July 14, 1971, Pat. No. 3,859,282, and Ser. No. 179,559, Sept. 10, 1971, abandoned.

[52] U.S. Cl. ............................. 260/243 C; 424/246
[51] Int. Cl.² ..................................... C07D 501/60
[58] Field of Search ............................... 260/243 C

[56] References Cited
UNITED STATES PATENTS

| | | |
|---|---|---|
| 3,705,897 | 12/1972 | Murphy ........................... 260/243 C |
| 3,709,880 | 1/1973 | Goegelman et al. ............ 260/243 C |
| 3,719,563 | 3/1973 | Hamill et al. ............... 260/243 C X |

OTHER PUBLICATIONS

Nagarajan et al., J. Am. Chem. Soc. 93(9) pp. 2308–2310 (5/5/71).

*Primary Examiner*—Nicholas S. Rizzo
*Assistant Examiner*—Diana G. Rivers
*Attorney, Agent, or Firm*—Richard A. Thompson; Julian S. Levitt

[57] ABSTRACT

Process for preparing an ester of 3-substituted methyl-7-acylamido-7-methoxy(or hydrogen)-2-cephem-4-carboxylic acid and its corresponding sulfoxide by treating an ester of 3-carbamoyloxymethyl(or 3-lower alkanoyloxymethyl)-7-acylamido-7-methoxy(or hydrogen)-2-cephem-4-carboxylic acid with a hydrohalic acid or another compound containing an active hydrogen and then with an oxidizing agent. The products obtained are useful as intermediates in the preparation of antibiotics.

6 Claims, No Drawings

3-SUBSTITUTED METHYL-7-ACYLAMINO-7-METHOXY-2-CEPHEM-4-CARBOXYLIC ACID AND ITS ESTERS

This is a division of application Ser. No. 201,210 filed Nov. 22, 1971, now abandoned, which is a Continuation-in-part of applicants' co-pending U.S. application Ser. No. 162,703, filed July 14, 1971, now issued as U.S. Pat. No. 3,859,282, and U.S. Ser. No. 179,559, filed Sept. 10, 1971, now abandoned.

This invention relates to a novel process for preparing an ester of 3-substituted methyl-7-acylamido-7-methoxy(or hydrogen)-2-cephem-4-carboxylic acid (I, infra). This invention also relates to the preparation of novel 3-substituted methyl-7-acylamido-7-methoxy-2-cephem-4-carboxylic acids and esters and the corresponding sulfoxides.

The products are useful as intermediates in the preparation of known cephalosporin compounds and also the recently discovered cephalosporins having a methoxy substituent in the 7-position in place of the hydrogen substituent of the known cephalosporins. The cephalosporin products which may be prepared from these novel intermediates are useful as antibiotics against gram-positive and gram-negative microorganisms.

Cephalosporins having a 7-methoxy substituent are effective against gram-negative bacteria including *Escherichia coli, Proteus vulgaris, Proteus mirabilis, Proteus morganii, Salmonella schottmuelleri, Klebsiella pneumoniae AD, Klebsiella pneumoniae B*, and *Paracolobactrum arizoniae* and gram positive bacteria including *Staphylococcus aureus, Streptococcus pyogenes* and *Diplococcus pneumoniae*.

The 7-methoxy cephalosporins are useful in removing susceptible microorganisms from pharmaceutical, medical and dental equipment and as bactericides in industrial applications, for example, in water based paints and in the white water of paper mills to inhibit the growth of harmful bacteria.

This invention comprises treating an ester of 3-carbamoyloxymethyl(or 3-lower alkanoyloxymethyl)-7-acylamido-7-methoxy(or hydrogen)-2-cephem-4-carboxylic acid (II, infra) with a hydrohalic acid, for example, hydrobromic acid, hydrochloric acid, hydroiodic acid and the like. Alternatively, in lieu of the hydrohalic acid there may be employed another compound having an active hydrogen. This reaction with the compound having an active hydrogen is conducted in the presence of a catalyst, for example, a non-nucleophilic acid or a Lewis acid. Compounds having an active hydrogen are well known in the art and the following examples are merely illustrative of the type of compound which may be employed; inorganic acids such as hydrazoic acid and the like, organic acids, for example, lower alkanoic acid such as acetic acid, propionic acid, butyric acid and the like, arylcarboxylic acids such as benzoic acid and the like, haloacetic acids such as trifluoroacetic acid and the like, mono- or polyhydroxybenzenes such as phenol, resorcinol and the like or alkyl-3-oxoalkanoate, for example, lower alkyl-3-oxo lower alkanoate such as ethyl-3-oxobutanoate, methyl-3-oxobutanoate, ethyl-3-oxopentanoate and the like.

To increase the reactivity of these active hydrogen-containing compounds a catalyst is employed in the reaction; for example, non-nucleophilic acids such as perchloric acid, benzenesulfonic acid and the like or a Lewis acid such as boron trifluoride, boron trichloride, aluminum chloride and the like.

The reaction with either the hydrohalic acid or other compound containing an active hydrogen may be conducted in any solvent in which the reactants are soluble and inert or substantially inert such as methylene chloride, tetrahydrofuran, chloroform, carbon tetrachloride, benzene, hexane, diethyl ether and the like. The reaction may be conducted at a temperature in the range of from about −70° C. to about 100° C. In general, the reaction is conducted at a temperature in the range of from about 0° C. to about 5° C. The reaction time naturally varies with the temperature at which the reaction is conducted and may vary from about 5 minutes up to about 25 hours; however, at a temperature in the range of 0° C. to about 5° C., the reaction is usually complete within 15 hours. The following equation illustrates this process:

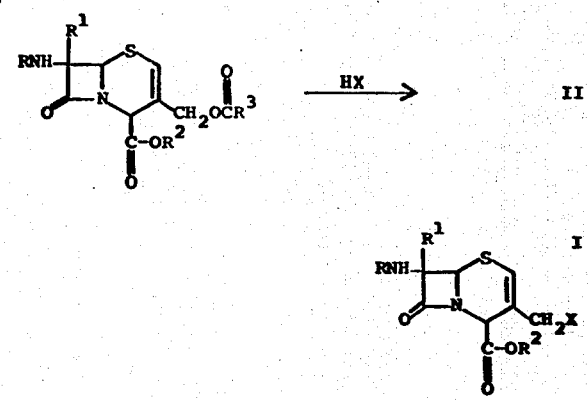

wherein R is acyl; $R^1$ is hydrogen or methoxy; $R^2$ is a protecting group; $R^3$ is amino or methyl, and X is halo such as bromo, chloro, iodo and the like, azido, lower alkanoyloxy such as acetoxy, propionyloxy, butyryloxy and the like, aroyloxy such as benzoyloxy and the like, a mono- or polyhydroxyphenyl such as 4-hydroxyphenyl, 2,4-dihydroxyphenyl and the like or a 1-alkoxycarbonyl-2-oxoalkyl, for example, a 1-lower alkoxycarbonyl-2-oxo lower alkyl compound of the formula:

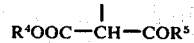

wherein $R^4$ and $R^5$ are the same or different alkyl radicals, for example lower alkyl radicals containing from 1–4 carbon atoms such as methyl, ethyl, n-propyl, n-butyl and the like.

The acyl radical, R, may be any one of the acyl functions presently known in the cephalosporin art. For example, R may be an acyl radical of the formula:

wherein $R^6$ is benzyl, p-hydroxybenzyl, α-aminobenzyl, α-carboxybenzyl, α-azidobenzyl, allylthiomethyl, butylmercaptomethyl, D-(or L)-4-amino-4-carboxybutyl, α-chloro-n-heptyl, ethyl, 3- or 5-nitrobenzyl, phenethyl, β,β-diphenethyl, thienyl, phenylthiomethyl, 2-thenyl, α-amino-2-thienylmethyl, α-methylaminobenzyl, α-(N-methylsulfamyl)benzyl, D(—)-α-guanidino-2-thienylmethyl, D(—)-α-guanidinobenzyl, 4-guanidinophenoxymethyl, 4-guanidinomethylbenzyl, cyanomethyl, 2,6-dimethoxy-4-guanidinophenyl, 2- or 3-furylmethyl, 1-H-tetrazol-1-yl methyl and the like.

In carrying out the reactions described herein, it is preferred to protect the 4-carboxy group and also other groups in the nucleus which need protection, for example, other carboxy groups, amino groups or hydroxy groups. Maximum yields are obtained by employing these protected compounds. Naturally, the groups which are preferred are those which are easily removed. Examples of these protecting groups, $R^2$ in the formulas, are trichloroethyl, tertbutyl, benzoylmethyl, p-methoxybenzyl, benzyl, benzhydryl, methoxymethyl and the like. Amino groups can be protected by trichloroethoxycarbonyl, tert-butoxycarbonyl p-chlorobenzoyloxycarbonyl and the like.

The ester of 3-halomethyl-7-acylamido-7-methoxy-(or hydrogen)-2-cephem-4-carboxylic acid (Ia) obtained above provides a convenient starting point for preparing other 3-substituted methyl derivatives. The 3-halomethyl derivative (Ia) may be converted to other 3-substituted methyl compounds (III) by treating the 3-halomethyl compound with water, a lower alkanol, for example, methanol, ethanol, propanol and the like, a metal cyanide, for example, cuprous cyanide and the like, an alkali metal salt of a carboxylic acid, for example, an alkali metal salt of a lower alkanoic acid such as acetic acid, propionic acid, butyric acid and the like, an alkali metal salt of an aryl carboxylic acid, for example, an alkali metal salt of benzoic acid and the like or an alkaline earth metal salt of carbamic acid such as calcium carbamate and the like. The reaction may be conducted at a temperature in the range of from about 20° to about 100° C. In general, the reaction is conducted at a temperature in the range of from about 0° to 25° C. Any solvent which is inert or substantially inert to the reactants may be employed, for example, dimethylformamide, p-dioxane, dimethylsulfoxide, acetonitrile, tetrahydrofuran and the like. The following equation illustrates this reaction:

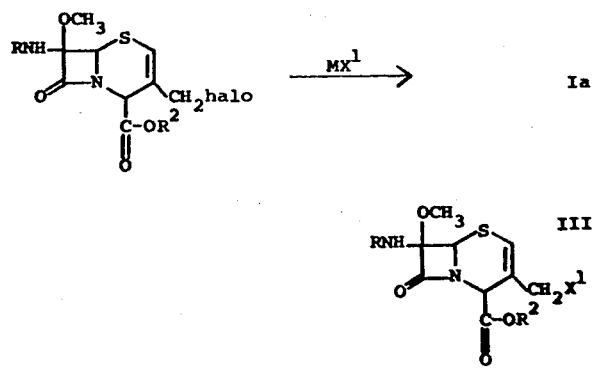

wherein R, $R^2$ and halo are as defined above and $X^1$ is lower alkoxy, for example, methoxy, ethoxy, n-propoxy and the like, cyano, hydroxy, lower alkanoyloxy such as acetoxy, propionyloxy, butyryloxy and the like, aroyloxy, for example, benzoyloxy and the like, carbamoyloxy, heterocyclic thio, for example, a 5-membered heterocyclic containing two nitrogen hetero atoms and one sulfur hetero atom such as 5-methyl-1,3,4-thiadiazolyl-2-thio, a tertiary amine such as pyridine and the like, heterocyclic thiocarbonylthio, for example, a 6-membered nitrogen containing heterocyclic thiocarbonylthio such as piperidinothiocarbonylthio, and M is hydrogen, a cation derived from an alkali metal or alkaline earth metal such as sodium, potassium, calcium and the like or a cation derived from a Group IB metal such as copper and the like.

The ester of 3-halomethyl-7-acylamido-7-methoxy-2-cephem-4-carboxylic acid (Ia) may be converted to the corresponding 3-methyl compound by treatment with a reducing agent such as zinc dust in a suitable inert solvent or mixture of inert solvents such as a dioxane and acetic acid.

The ester of the 3-substituted methyl-7-acylamido-7-methoxy-2-cephem-4-carboxylic acids (V) may be converted to its corresponding sulfoxide (IV, infra) by treatment with an oxidizing agent, for example, a peracid such as m-chloroperbenzoic acid, periodic acid, perphthalic acid, peracetic acid, perbenzoic acid, pertrifluoroacetic acid, performic acid and the like or with a salt of a peracid, for example, an alkali metal salt of periodic acid such as sodium periodate and the like or with hydrogen peroxide. The oxidation is conducted in an inert solvent such as methylene chloride, carbon tetrachloride, chloroform, benzene, the lower alkanols such as methanol, ethanol and the like, acetone or water at a temperature in the range of from about —20° C. to about 50° C. and preferably at about 0° C. The following equation illustrates this process:

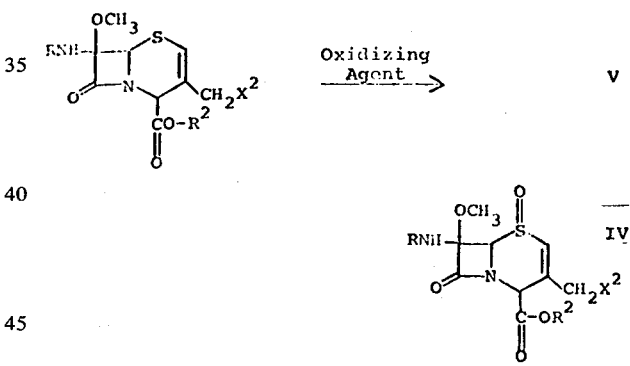

wherein R, $R^2$ and Y are as defined above and $X^2$ is hydrogen, halo, cyano, lower alkoxy, hydroxy, carbamoyloxy, lower alkanoyloxy, aroyloxy, mono-, polyhydroxyphenyl, 1-alkoxycarbonyl-2-oxoalkyl, heterocyclic thio, a tertiary amine or heterocyclicthiocarbonylthio.

The product (IV) of the oxidation step may also contain some of the Δ³-cephem compound. When an alcohol is employed as the solvent in the oxidation reaction or when the oxidizing agent employed is an acid, the product obtained is generally a mixture of the Δ² and Δ³ cephems. This mixture is converted to the Δ³-cephem compound by the isomerization procedure described below.

The ester of the 3-substituted methyl-7-acylamido-7-methoxy-2-cephem-4-carboxy-1-oxide (IV, supra) can then be converted to the corresponding Δ³-cephem compound (VI, infra) by treating the Δ² sulfoxide with an isomerizing agent, for example, an alcohol or an organic base or an adsorbent such as alumina, silica gel and Florisil and the like and then treating the $\Delta^3$ sulfoxide (VI) with a reducing agent such as stannous chloride and the like to obtain the ester of the 3-substituted methyl-7-acylamido-7-methoxy-3-cephem-4-carboxylic acid (VII, infra). The following equation illustrates this process.

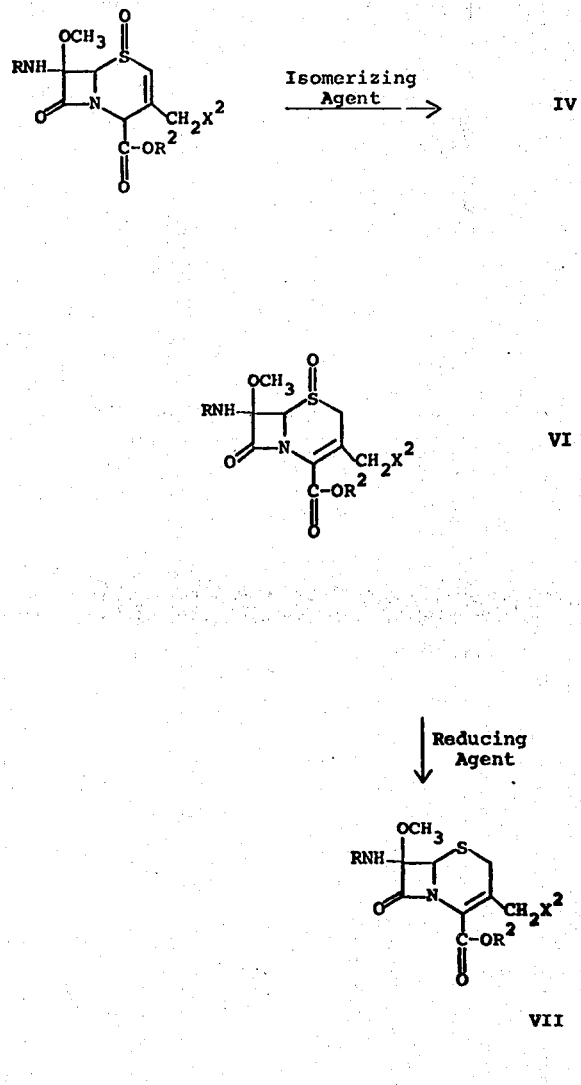

wherein R, $R^2$ and $X^2$ are as defined above.

The 3-carbamoyloxymethyl(or 3-lower alkanoyloxymethyl)-7-acylamido-7-methoxy(or hydrogen)-2-cephem-4-carboxylic acid (II, supra) described above are prepared by the isomerization of the corresponding pure $\Delta^3$-cephem compound (VIII, infra) or a mixture of the $\Delta^2$ and $\Delta^3$ isomeric cephems by treating the $\Delta^3$-cephem compound, or the isomeric mixture, with an isomerizing agent. This may be accomplished by dissolving the $\Delta^3$-cephem compound, or the mixture, (VIII) in an appropriate solvent, for example, a lower alkanol such as methanol, ethanol and the like, a polyhalo lower alkyl such as chloroform, methylene chloride and the like, an aromatic solvent such as benzene and the like, lower alkyl esters such as ethylacetate and the like or ethers such as diethyl ether and the like or mixtures of these solvents and treating these solutions with Florisil, silica gel, alumina and the like or by treating the $\Delta^3$-cephem compound or the mixture (VIII) with a base, for example, an organic base such as pyridine or a trialkylamine such as triethylamine and the like or inorganic base, for example, an alkali or alkaline earth metal hydroxide, alkoxide and the like such as sodium hydroxide, potassium hydroxide, aluminum hydroxide, sodium methoxide, sodium ethoxide and the like. The following equation illustrates this reaction employing the $\Delta^3$-cephem compound; however, employing a mixture of the $\Delta^2$ and $\Delta^3$-cephem compound will afford similar results:

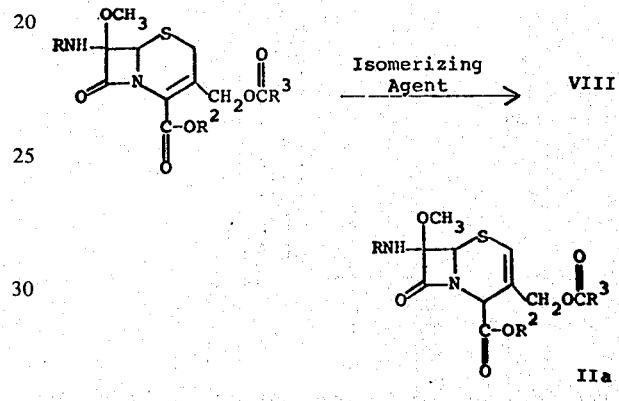

wherein R, $R^2$ and $R^3$ are as defined above.

Those compounds (VIII) having an acyl radical other than a 7$\beta$-(D-5-carboxyvaleryl) radical are prepared by treating compound VIIIa with an acylating agent in a suitable solvent such as chloroform, dioxane, methylene chloride, acetonitrile and the like in the presence of a silyl compound, for example, a trialkylated silane trifluoroacetamide such as N-trimethylsilyl trifluororacetamide and the like at a temperature in the range of from about room temperature up to about 50° C. The 7$\beta$-(D-5-amino-5-carboxyvaleryl) group is then removed by removal of the protecting group ($R^2$) which results in the cleavage of the 7$\beta$-(D-5-amino-5-carboxyvaleryl) group. The following equation illustrates this process:

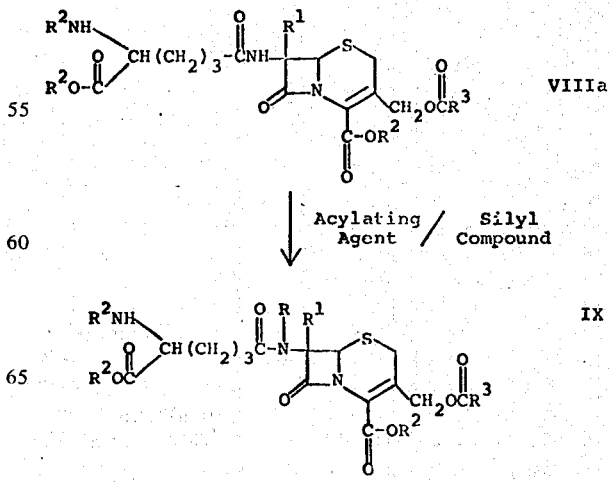

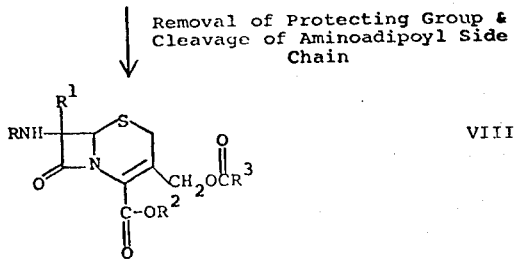

wherein R, $R^1$, $R^2$ and $R^3$ are as defined above.

The compound 7-(D-5-amino-5-carboxyvaleramido)-3-carbamoyloxymethyl-7-methoxy-3-cephem-4-carboxylic acid was originally isolated as a single colony from soil on an agar slant and is obtained by fermentation process. A sample of the microorganism affording said compound is on permanent deposit with a culture collection of the Northern Utilization Research and Development Branch of the U.S. Department of Agriculture at Peoria, Illinois, and has been assigned the culture number NRRL-3802 and is identified in the Merck deposit collection as MA-2908. The 7β-(D-5-amino-5-carboxyvaleramido)-3-(carbamoyloxymethyl)-7-methoxy-3-cephem-4-carboxylic acid is produced during the aerobic fermentation of suitable aqueous nutrient mediums under controlled conditions via inoculation with the organism *Streptomyces lactamdurans* (NRRL-3802). In general, any medium which is a source of carbon and nitrogen may be employed. The exact amount of the carbohydrate and nitrogen sources will depend on the other ingredients comprising the fermentation medium but, in general, the amount of carbohydrate is usually about 1% to 6% by weight of the medium and the amount of available nitrogen, either alone or in combination, is usually in the amount of from about 0.2% to about 6% by weight of the medium. The medium described below is illustrative of a medium which is suitable for the preparation; however, it should be understood that other media may be employed.

Medium:
1% Blackstrap Molasses
1% National Brewer's Yeast
2.5% Difco agar pH 7.0
Water to volume The fermentation is carried out at a temperature in the range of from about 20° C. to about 37° C. but for optimum results it is preferable to conduct the fermentation at a temperature in the range of from about 24° C. to 32° C. The pH of the nutrient medium suitable for growing the Streptomyces lactamdurans culture and for producing 7β-(D-5-amino-5-carboxyvaleramido)-3-(carbamoyloxymethyl)-7-methoxy-3-cephem-4-carboxylic acid should be in the range of from about 6.0 to about 8.0.

The 7β-(D-5-amino-5-carboxyvaleramido)-3-carbamoyloxymethyl-7-methoxy-3-cephem-4-carboxylic acid is recovered from the fermentation broth by passing the filtered broth at pH 7.0 over a strongly basic anion exchange resin eluting the product from the resin with 3% ammonium chloride in 90% methanol, repeating the adsorption at pH 7.2 to 8.0, eluting with 5% aqueous sodium chloride, adsorbing the active eluates at pH 2.0 on a strongly acidic cation exchanger of the sulfonate type, eluting the product with a 2% aqueous pyridine solution and recovering the pyridinium salt which salt can be converted to other salts or to the free acid in accordance with procedures well known in this art.

The blocking and protecting groups, $R^2$, employed above, can be removed at any time in the process to afford those compounds wherein $R^2$ would be hydrogen. For example, the ester group is removed to afford the free acid. These groups may be removed by methods well known to those skilled in the art, for example, the trichloroethoxycarbonyl group is removed by treatment with zinc dust or chromous chloride using alcohols such as methanol, ethanol, propanol, butanol and the like or acetic acid or a mixture of acetic acid and water as a solvent. In addition, the blocking groups such as benzhydryl, phenylalkyl, tert-butyl or methoxymethyl may be removed by treatment with hydrogen in the presence of a catalyst such as palladium on carbon or with a strong organic or inorganic acid such as hydrochloric acid, sulfuric acid, boron trifluoride etherate, formic acid, trifluoroacetic acid, trichloroacetic acid, nitrobenzoic acid and the like.

The following examples illustrate the novel process of this invention. However, the examples are illustrative only and it will be apparent to those skilled in the art that other reagents similar to those described in the following examples may be employed to afford similar results.

EXAMPLE 1

Benzhydryl ester of 7-methoxy-3-methoxymethyl-7-(2-thienylacetamido)-2-cephem-4-carboxy-1-oxide Step A: Benzhydryl ester of 3-carbamoyloxymethyl-7-methoxy-7-(2-thienylacetamido)-2-cephem-4-carboxylic Acid The benzhydryl ester of 3-carbamoyloxymethyl-7-methoxy-7-(2-thienylacetamido)-3-cephem-4-carboxylic acid (1.0 g.) is applied on a column of Florisil (20.0 g.) packed with benzene. A solution of 10% ethyl acetate in benzene is allowed to drip through the column overnight. The $\Delta^2$-isomer thus formed is eluted with 40% ethyl acetate in benzene. After evaporation the product is found to be pure and has the following physical characteristics.

NMR: (Solvent - CDCl$_3$) δ=6.32 (2-H, d, $J_{AB}$=2Hz), 5.10 (4-H, d, $J_{AB}$=2Hz), 5.32 (6-H), 3.40 (7-OCH$_3$, s), 4.52 (10-H$_2$, s), 3.82 (23-H$_2$, s).

Step B: Benzhydryl ester of 3-bromoethyl-7-methoxy-7-(2-thienylacetamido)-2-cephem-4-carboxylic Acid In a system void of atmospheric moisture, a saturated solution of hydrogen bromide (0.0132 mole) in methylene chloride (110.0 ml.) is added dropwise to a stirred, cold (in ice) solution of benzhydryl ester of 3-carbamoyloxymethyl-7-methoxy-7-(2-thienylacetamido)-2-cephem-4-carboxylic acid (0.0056 mole) in methylene chloride (40.0 ml.). After the addition is over, the reaction mixture is condensed to 30 ml. and is used directly in the next step.

Step C: Benzhydryl ester of 7-methoxy-3-methoxymethyl-7-(2-thienylacetamido)-2-cephem-4-carboxylic Acid The methylene chloride solution of the benzhydryl ester of 3-bromoethyl-7-methoxy-7-(2-thienylacetamido)-2-cephem-4-carboxylic acid from Step G, and calcium carbonate (29.5 g.) is stirred at 0° C. while methanol (50.0 ml.) is added dropwise. The mixture is stirred for another 1½ hours and is worked up by partition between methylene chloride and a 5% aqueous sodium bicarbonate solution. The organic layer is washed with water, dried over sodium sulfate and evaporated to give 3 g. of crude product. This is purified by column chromatography to yield 2.3 g. of pure benzhydryl ester of 7-methoxy-3-methoxymethyl-7-(2-thienylacetamido)-2-cephem-4-carboxylic acid.

NMR: (Solvent - $CDCl_3$) $\delta=6.2$ (2-H, d, J=2Hz), 5.1 (4-H, d, J=2Hz), 5.38 (6H, s), 3.39 (7-$OCH_3$, s), 3.8 (10-$H_2$, s), 3.1 (10-$OCH_3$, s), 3.82 (13-$H_2$, $J_{AB}=10Hz$).

Step D: Benzhydryl ester of 7-methoxy-3-methoxymethyl-7-(2-thienylacetamido)-2-cephem-4-carboxy-1-oxide To a stirred, cooled (in ice) solution of benzhydryl ester of 7-methoxy-3-methoxymethyl-7-(2-thienylacetamido)-2-cephem-4-carboxylic acid (2.3 g.) in 50 ml. of a 1:1 mixture of methylene chloride and isopropanol is added dropwise a solution of m-chloroperbenzoic acid (1.0 g.) in methylene chloride (25 ml.). After stirring an hour in ice and an additional ½ hour at room temperature, the reaction mixture is washed successively with a sodium bicarbonate solution, water and saturated sodium chloride solution. The organic solution is evaporated to give 1.0 g. of benzhydryl ester of 7-methoxy-3-methoxymethyl-7-(2-thienylacetamido)-2-cephem-4-carboxy-1-oxide which also contains the $\Delta^3$ cephem isomer.

EXAMPLE 2

Dibenzhydryl ester of 7β-(D-5-trichloroethoxycarbonylamino-5-carboxyvaleramido)-3-cyanomethyl-7-methoxy-2-cephem-4-carboxy-1-oxide Step A: Dibenzhydryl ester of 7β-(D-5-trichloroethoxycarbonylamino-5-carboxyvaleramido)-3-carbamoyloxymethyl-7-methoxy-2-cephem-4-carboxylic Acid The dibenzhydryl ester of 7β-(D-5-trichloroethoxycarbonylamino-5-carboxyvaleramido)-3-carbamoyloxymethyl-7-methoxy-3-cephem-4-carboxylic acid (10 g.) is slowly eluted through a Florisil column (200 g.) with a 10% solution of ethyl acetate in benzene. The $\Delta^2$ compound thus formed is then removed from the column with a 40% solution of ethyl acetate in benzene. Removal of the solvent yields the substantially pure dibenzhydryl ester of 7β-(D-5-trichloroethoxycarbonylamino-5-carboxyvaleramido)-3-carbamoyloxymethyl-7-methoxy-2-cephem-4-carboxylic acid (6.5 g.). This material shows a single spot on thin layer chromatography.

UV: $\lambda$max. ($CH_3OH$) 247.5 $\epsilon$7200

NMR: (Solvent - $CDCl_3$) $\delta=3.41$ (7-$CH_3O$, s), 4.72 (10-H, s), 5.34 (6-H, s), 6.3 (2-H, d, $J_{AB}=1.5Hz$), 5.16 (4-H, d, $J_{AB}=1.5Hz$).

Step B: Dibenzhydryl ester of 7β-(D-5-trichloroethoxycarbonylamino-5-carboxyvaleramido)-3-(bromomethyl)-7-methoxy-2-cephem-4-carboxylic Acid To a cold solution (in ice) of the dibenzhydryl ester of 7β-(D-5-trichloroethoxycarbonylamino-5-carboxyvaleramido)-3-carbamoyloxymethyl-7-methoxy-2-cephem-4-carboxylic acid (15.0 g.) in methylene chloride (150 ml.) is added dropwise hydrogen bromide in methylene chloride (60 ml., 0.57 N). The mixture is stirred at 0°–5° C. for one hour. The reaction is stopped by bubbling off the excess hydrogen bromide with nitrogen. The white precipitate of ammonium bromide is removed by filtration. The reaction mixture is extracted twice with cold water, dried and evaporated to yield 21.6 g. of the crude dibenzhydryl ester of 7β-(D-5-trichloroethoxycarbonylamino-5-carboxyvaleramido)-(3-bromomethyl)-7-methoxy-2-cephem-4-carboxylic acid. It is about 80% pure as indicated by the NMR spectrum.

NMR: (Solvent - $CDCl_3$) $\delta=3.42$ (7-$CH_3O$, s), 4.07 (10-$H_2$, q), 5.35 (6-H, s), 6.3 (2-H, d, $J_{AB}=2Hz$), 5.35 (4-H, d, $J_{AB}=2Hz$).

Step C: Dibenzhydryl ester of 7β-(D-5-trichloroethoxycarbonylamino-5-carboxyvaleramido)-(3-cyanomethyl)-7-methoxy-2-cephem-4-carboxylic Acid The dibenzhydryl ester of 7β-(D-5-trichloroethoxycarbonylamino-5-carboxyvaleramido)-(3-bromomethyl)-7-methoxy-2-cephem-4-carboxylic acid (5.0 g.) is dissolved in dimethylsulfoxide (100 ml.). The solution is cooled to 10°–15° C. To this is slowly added cuprous cyanide (0.6 g.). The reaction mixture is allowed to warm up to room temperature and is stirred for another six hours. The reaction mixture is then partitioned between methylene chloride and water. The methylene chloride layer is dried over anhydrous sodium sulfate, filtered and the solvent removed by evaporation. Purification by column chromatography using silica gel H with chloroform as the eluant yields the dibenzhydryl ester of 7β-(D-5-trichloroethoxycarbonylamino-5-carboxyvaleramido)-(3-cyanomethyl)-7-methoxy-2-cephem-4-carboxylic acid. Thin layer chromatography shows a single spot.

UV: $\lambda$max. ($CH_3OH$) 2480 $\epsilon$6900

NMR: (Solvent - $CDCl_3$) $\delta=3.42$ (7-$CH_3O$, s), 3.17 (10-$H_2$, s), 5.33 (6-H, s), 6.27 (2-H, d, $J_{AB}=2HZ$), 5.05 (4-H, d, $J_{AB}=2Hz$).

Step D: Dibenzhydryl ester of 7β-(D-5-trichloroethoxycarbonylamino-5-carboxyvaleramido)-3(cyanomethyl)-7-methoxy-2-cephem-4-carboxy-1-oxide An ice cold solution of dibenzhydryl ester of 7β-(D-5-trichloroethoxycarbonylamino-5-carboxyvaleramido)-3-(cyanomethyl)-7-methoxy-2-cephem-4-carboxylic acid (3.04 mmoles) in methylene chloride (20 ml.) is added dropwise a solution of m-chloroperbenzoic acid (0.6 g., 3.0 mmoles) in methylene chloride (20 ml.). After one hour the reaction mixture is washed with an aqueous sodium bicarbonate solution and then with water. The reaction mixture is dried over sodium sulfate, filtered and the solvent is removed to afford dibenzhydryl ester of 7β-(D-5-trichloroethoxycarbonylamino-5-carboxyvaleramido)-3-(cyanomethyl)-7-methoxy-2-cephem-4-carboxy-1-oxide.

EXAMPLE 3

Benzyl ester of 3-methoxymethyl-7-(2-thienylacetamido)-2-cephem-4-carboxy-1-oxide Step A: Benzyl ester of 3-acetoxymethyl-7-(2-thienylacetamido)-2-cephem-4-carboxylic Acid The benzyl ester of 3-acetoxymethyl-7-(2-thienylacetamido)-3-cephem-4-carboxylic acid (100 mg.) is applied on a Florisil (2 g.) column packed with benzene. A solution of 10% ethylacetate in benzene is allowed to drop through the column overnight. The $\Delta^2$-isomer thus formed is eluted with a mixture of ethylacetate and benzene (3:10). Evaporation of the solvent affords 82 mg. of pure benzyl ester of 3-acetoxymethyl-7-(2-thienylacetamido)-2-cephem-4-carboxylic acid. Thin layer chromatography shows a single spot.

NMR: (Solvent - CDCl$_3$) δ=5.58 (7-H, q), 5.2 (6-H, d), 6.37 (2-H, d, J$_{AB}$=1Hz), 5.01 (4H, d, J$_{AB}$=1Hz), 4.58 (10-H$_2$, s), 3.80 (13-H$_2$, s), 1.97

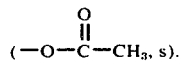

$(-O-\overset{\overset{O}{\|}}{C}-CH_3, s)$.

Step B: Benzyl ester of 3-bromomethyl-7-(2-thienylacetamido)-2-cephem-4-carboxylic Acid A cooled solution (in ice) of benzyl ester of 3-acetoxymethyl-7-(2-thienylacetamido)-2-cephem-4-carboxylic acid (77 mg., 0.15 mmole) is stirred while hydrogen bromide (0.5 ml.) in methylene chloride (0.32 mmole) is added dropwise. The reaction is stopped 50 minutes later by simply bubbling off the excess hydrogen bromide with nitrogen. Removal of the solvent affords the benzyl ester of 3-bromomethyl-7-(2-thienylacetamido)-2-cephem-4-carboxylic acid which is employed directly in Step C.

Step C: Benzyl ester of 3-methoxymethyl-7-(2-thienylacetamido)-2-cephem-4-carboxylic Acid The benzyl ester of 3-bromomethyl-7-(2-thienylacetamido)-2-cephem-4-carboxylic acid is dissolved in methanol. After standing at room temperature for 20 minutes the reaction mixture is poured into a dilute sodium bicarbonate solution and extracted with methylene chloride. The organic layer is washed with aqueous sodium chloride and dried. Removal of the solvent affords 35 mg. of crude product. The pure benzyl ester of 3-methoxymethyl-7-(2-thienylacetamido)-2-cephem-4-carboxylic acid is then isolated by preparative thin layer chromatography (15% ethyl acetate in chloroform as eluant).

NMR: (Solvent - CDCl$_3$) δ=5.61 (7-H, q), 5.21 (6-H, d), 6.25 (2-H, d, J$_{AB}$=1Hz), 5.02 (4H, d, J$_{AB}$=1Hz), 5.17 (10-H$_2$, partially visible), 3.82 (13-H$_2$, s), 3.18 (-OCH$_3$, s).

Step D: Benzyl ester of 3-methoxymethyl-7-(2-thienylacetamido)-2-cephem-4-carboxy-1-oxide By substituting for the dibenzhydryl ester of 7β-(D-5-trichloroethoxycarbonylamino-5-carboxyvaleramido)-3-(cyanomethyl)-7-methoxy-2-cephem-4-carboxylic acid of Example 2, Step D, the benzyl ester of 3-methoxymethyl-7-(2-thienylacetamido)-2-cephem-4-carboxylic acid and following substantially the procedure described therein, there is obtained the benzyl ester of 3-methoxymethyl-7-(2-thineylacetamido)-2-cephem-4-carboxy-1-oxide.

EXAMPLE 4

Dibenzhydryl ester of 7β-(D-5-trichloroethoxycarbonylamino-5-carboxyvaleramido)-3-(4-hydroxybenzyl)-7-methoxy-2-cephem-4-carboxy-1-oxide.

Step A: Dibenzhydryl ester of 7β-(D-5-trichloroethoxycarbonylamino-5-carboxyvaleramido)-3-(4-hydroxybenzyl)-7-methoxy-2-cephem-4-carboxylic Acid A solution of the dibenzhydryl ester of 7β-(D-5-trichloroethoxycarbonylamino-5-carboxyvaleramido)-3-carbamoyloxymethyl-7-methoxy-2-cephem-4-carboxylic acid (0.953 g., 1 mmole), phenol (1.4 g., 1.1 mmole) and 70% perchloric acid (1.1 mmole) in methylene chloride (20 ml.) and tetrahydrofuran (11 ml.) is stirred for 5 hours at 0° C. The reaction mixture is washed with a sodium bicarbonate solution and then with water. The reaction mixture is dried over sodium sulfate, filtered and the solvent removed to afford the crude product. The crude product is purified by elution through a column containing silica gel employing a solution of chloroform and ethyl acetate (8:2) as the eluant to afford dibenzhydryl ester of 7β-(D-5-trichloroethoxycarbonylamino-5-carboxyvaleramido)-3-(4-hydroxybenzyl)-7-methoxy-2-cephem-4-carboxylic acid. This product shows a single spot on thin layer chromatography.

NMR: (Solvent - CDCl$_3$) δ=5.78 (2-H, d, J$_{AB}$=1Hz), 4.8 (4-H, d, J$_{AB}$=1Hz), 5.4 (6-H, s), 3.37 (7-OCH$_3$, s), 3.3 (10-H$_2$, partially visible), 6.85 [phenol (4Hs), q, J$_{AB}$=10Hz].

Step B: Dibenzhydryl ester of 7β-(D-5-trichloroethoxycarbonylamino-5-carboxyvaleramido)-3-(4-hydroxybenzyl)-7-methoxy-2-cephem-4-carboxy-1-oxide An ice cold solution of dibenzhydryl ester of 7β-(D-5-trichloroethoxycarbonylamino-5-carboxyvaleramido)-3-(4-hydroxybenzyl)-7-methoxy-2-cephem-4-carboxylic acid (3.0 g., 3.04 mmoles) in methylene chloride (20 ml.) is added dropwise a solution of m-chloroperbenzoic acid 0.6 g., 3.0 mmoles) in methylene chloride (20 ml.). After one hour the reaction mixture is washed with an aqueous sodium bicarbonate solution and then with water. The reaction mixture is dried over sodium sulfate, filtered and the solvent is removed to afford the dibenzhydryl ester of 7β-(D-5-trichloroethoxycarbonylamino-5-carboxyvaleramido)-3-(4-hydroxybenzyl)-7-methoxy-2-cephem-4-carboxy-1-oxide along with some of the Δ$^3$ cephem compound.

EXAMPLE 5

Dibenzhydryl ester of 7β-(D-5-trichloroethoxycarbonylamino-5-carboxyvaleramido)-3-(2-ethoxycarbonyl-3-oxobutyl)-7-methoxy-2-cephem-4-carboxy-1-oxide Step A: Dibenzhydryl ester of 7β-(D-5-trichloroethoxycarbonylamino-5-carboxyvaleramido)-3-(2-ethoxycarbonyl-3-oxobutyl)-7-methoxy-2-cephem-4-carboxylic Acid To a solution of the dibenzhydryl ester of 7β-(D-5-trichloroethoxycarbonylamino-5-carboxyvaleramido)-3-carbamoyloxymethyl-7-methoxy-2-cephem-4-carboxylic acid (0.425 g.) in methylene chloride (5.0 ml.) is added a solution of ethyl-acetoacetate (0.07 ml.) and boron trifluoride etherate (0.08 ml.) in methylene chloride (1 ml.). The reaction mixture is stirred for 2 hours and then diluted with ethyl acetate (100 ml.). The solution is washed with an aqueous sodium bicarbonate solution and then dried over anhydrous sodium sulfate. The solution is filtered and the solvent removed to afford crude product which is purified by chromatographing on a column containing silica gel G using chloroform as the eluant to afford dibenzhydryl ester of 7β-(D-5-trichloroethoxycarbonylamino-5-carboxyvaleramido)-3-(2-ethoxycarbonyl-3-oxobutyl)-7-methoxy-2-cephem-4-carboxylic acid. This product shows a single spot on thin layer chromatography.

Step B: Dibenzhydryl ester of 7β-(D-5-trichloroethoxycarbonylamino-5-carboxyvaleramido)-3-(2-ethoxycarbonyl-3-oxobutyl)-7-methoxy-2-cephem-4-carboxy-1-oxide By substituting for the dibenzhydryl ester of 7β-(D-5-trichloroethoxycarbonylamino-5-carboxyvaleramido)-3-(cyanomethyl)-7-methoxy-2-cephem-4-carboxylic acid of Example 2, Step D, an equimolar quantity of the dibenzhydryl ester of 7β-(D-5-trichloroethoxycarbonylamino-5-carboxyvaleramido)-3-(2-ethoxycarbonyl-3-oxobutyl)-7-methoxy-2cephem-4-carboxycarboxylic acid and by following substantially the procedure described therein, there is obtained the dibenzhydryl ester of 7β-(D-5-trichloroethoxycarbonylamino-5-carboxyvaleramido)-3-(2-ethoxycarbonyl-3-oxobutyl)-7-methoxy-2-cephem-4-carboxy-1-oxide.

EXAMPLE 6

Benzhydryl ester of 3-azidomethyl-7-methoxy-7-(2-thienylacetamido)-2-cephem-4-carboxylic Acid A mixture of the benzhydryl ester of 3-carbamoyloxymethyl-7-methoxy-7-(2-thienylacetamido)-2-cephem-4-carboxylic acid (0.212 g.), perchloric acid (0.36 g.) in tetrahydrofuran (6.0 ml.) and hydrazoic acid (28.0 ml., 0.18 N) in methylene chloride is stirred under a nitrogen atmosphere for nine hours. The reaction mixture is washed with a 5% aqueous sodium bicarbonate solution and then with a saturated sodium chloride solution. The methylene chloride solution is dried over anhydrous sodium sulfate, filtered and the solvent removed by evaporation. The crude product is purified by chromatographing through a column of silica gel G to yield the substantially pure benzhydryl ester of 3-azidomethyl-7-methoxy-7-(2-thienylacetamido)-2-cephem-4-carboxylic acid.

Elemental analysis for $C_{28}H_{25}N_5O_5S_2$:
Calc.: C, 58.4; H, 4.35; N, 12.32;
Found: C, 58.4; H, 4.72; N, 12.36.

EXAMPLE 7

Benzyl ester of 7-(D-5-trichloroethoxycarbonylamino-5-carboxyvaleramido)-(3-hydroxymethyl)-7-methoxy-2-cephem-4-carboxylic Acid A solution of the benzyl ester of 7-(D-5-trichloroethoxycarbonylamino-5-carboxyvaleramido)-(3-bromomethyl)-7-methoxy-2-cephem-4-carboxylic acid (0.7 g.) in 5 ml. of pH 7.5 buffer and 13.5 ml. of p-dioxane is allowed to stand at room temperature for 2 and ½ hours. The reaction mixture is extracted successively with ethyl acetate and the organic layer is washed with an aqueous saturated sodium chloride solution. After drying, the solvent is removed by evaporation and the product is purified by column chromatography [silica gel column with 2% methanol in a mixture of hexane and chloroform (1:1) as the eluant] to afford benzyl ester of 7-(D-5-trichloroethoxycarbonylamino-5-carboxyvaleramido)-(3-hydroxymethyl)-7-methoxy-2-cephem-4-carboxylic acid.

EXAMPLE 8

Dibenzhydryl ester of 7β-(D-5-trichloroethoxycarbonylamino-5-carboxyvaleramido)-3-benzoyloxymethyl-7-methoxy-2-cephem-4-carboxy-1-oxide Step A: Dibenzhydryl ester of 7β-(D-5-trichloroethoxycarbonylamino-5-carboxyvaleramido)-3-benzoyloxymethyl-7-methoxy-2-cephem-4-carboxylic Acid The dibenzhydryl ester of 7β-(D-trichloroethoxycarbonylamino-5-carboxyvaleramido)-3-bromomethyl-7-methoxy-2-cephem-4-carboxylic acid (1 mmole) in dimethylformamide (10 ml.) is added sodium benzoate (1 mmole). The reaction mixture is stirred at room temperature overnight. The reaction mixture is diluted with water and the product is extracted with methylene chloride. The methylene chloride solution is washed with an aqueous sodium bicarbonate solution and then with water. The solution is dried over magnesium sulfate, filtered and the solvent removed to afford dibenzhydryl ester of 7β-(D-5-trichloroethoxycarbonylamino-5-carboxyvaleramido)-3-benzoyloxymethyl-7-methoxy-2-cephem-4-carboxylic acid.

Step B: Dibenzhydryl ester of 7β-(D-5-trichloroethoxycarbonylamino-5-carboxyvaleramido)-3-benzoyloxymethyl-7-methoxy-2-cephem-4-carboxy-1-oxide By substituting for the dibenzhydryl estr of 7β-(D-5-trichloroethoxycarbonylamino-5-carboxyvaleramido)-3-(cyanomethyl)-7-methoxy-2-cephem-4-carboxylic acid of Example 2, Step D, the dibenzhydryl ester of 7β-(D-5-trichloroethoxycarbonylamino-5-carboxyvaleramido)-3-benzoyloxymethyl-7-methoxy-2-cephem-4-carboxylic acid and following the procedure described therein, there is obtained dibenzhydryl ester of 7β-(D-5-trichloroethoxycarbonylamino-5-carboxyvaleramido)-3-benzoyloxymethyl-7-methoxy-2-cephem-4-carboxy-1-oxide.

EXAMPLE 9

Benzhydryl ester of 3-Acetoxymethyl-7-methoxy-7-(2-thienylacetamido)-2-cephem-4-carboxy-1-oxide Step A: Benzhydryl ester of 3-acetoxymethyl-7-methoxy-7-(2-thienylacetamido)-2-cephem-4-carboxylic Acid A solution of the benzhydryl ester of 3-carbamoyloxy-7-methoxy-7-(2-thienylacetamido)-2-cephem-4-carboxylic acid (1 g.) in acetic acid (10 ml.) and 70% perchloric acid (0.5 ml.) is allowed to stand for ten hours at room temperature. The reaction mixture is then partitioned between water and ethyl acetate. The organic layer is washed with a sodium bicarbonate solution and then with water. The product is purified by chromatography on silica gel.

Step B: Benzhydryl ester of 3-Acetoxymethyl-7-methoxy-7-(2-thienylacetamido)-2-cephem-4-carboxy-1-oxide To a stirred, cooled (in ice) solution of benzhydryl ester of 3-acetoxymethyl-7-methoxy-7-(2-thienylacetamido)-2-cephem-4-carboxylic acid (2.3 g.)

in 50 ml. of a 1:1 mixture of methylene chloride and isopropanol is added dropwise a solution of m-chloroperbenzoic acid (1.0 g.) in methylene chloride (25 ml.). After stirring an hour in ice and an additional one-half hour at room temperature, the reaction mixture is washed successively with a sodium bicarbonate solution, water and saturated sodium chloride solution. The organic solution is evaporated to give 1.0 g. of the benzhydryl ester of 3-acetoxymethyl-7-methoxy-7-(2-thienylacetamido)-2-cephem-4-carboxy-1-oxide which also contains the Δ³-cephem isomer.

EXAMPLE 10

Benzhydryl ester of 3-Acetoxymethyl-7-methoxy-7-(2-thienylacetamido)-2-cephem-4-carboxy-1-oxide Step A: Benzhydryl ester of 3-acetoxymethyl-7-methoxy-7-(2-thienylacetamido)-2-cephem-4-carboxylic Acid A solution of benzhydryl ester of 3-bromomethyl-7-methoxy-7-(2-thienylacetamido)-2-cephem-4-carboxylic acid in methylene chloride (5 ml.) is added to a mixture of potassium acetate (0.5 g.) in acetic acid (10 ml.). After stirring overnight, the mixture is partitioned between ethyl acetate and water. The organic phase is dried (MgSO₄) and chromatographed to afford the product.

Step B: Benzhydryl ester of 3-Acetoxymethyl-7-methoxy-7-(2-thienylacetamido)-2-cephem-4-carboxy-1-oxide The benzhydryl ester of 3-acetoxymethyl-7-methoxy-7-(2-thienylacetamido)-2-cephem-4-carboxylic acid is oxidized by following the procedure of Example 9, Step B, to afford the benzhydryl ester of 3-acetoxymethyl-7-methoxy-7-(2-thienylacetamido)-2-cephem-4-carboxy-1-oxide.

EXAMPLE 11

Benzhydryl ester of 7-methoxy-3-methyl-7-(2-thienylacetamido)-2-cephem-4-carboxyl-1-oxide Step A: Benzhydryl ester of 7-methoxy-3-methyl-7-(2-thienylacetamido)-2-cephem-4-carboxylic Acid A solution of benzhydryl ester of 3-bromomethyl-7-methoxy-7-(2-thienylacetamido)-2-cephem-4-carboxylic acid (1 g.) in dioxane (10 ml.) and acetic acid (1 ml.) is agitated with 1 g. of zinc dust for two hours. The reaction mixture is filtered and the filtrate is partitioned between methylene chloride and sodium bicarbonate solution. Evaporation of the organic layer affords the product which is purified by chromatography.

Step B: Benzhydryl ester of 7-methoxy-3-methyl-7-(2-thienylacetamido)-2-cephem-4-carboxy-1-oxide To a stirred, cooled solution of the benzhydryl ester of 7-methoxy-3-methyl-7-(2-thienylacetamido)-2-cephem-4-carboxylic acid (2.0 g.) in a 1:1 mixture of methylene chloride and isopropanol (50 ml.) is added dropwise a solution of m-chloroperbenzoic acid (1.0 g.) in methylene chloride (25 ml.). After stirring for one hour in an ice bath the reaction mixture is allowed to come to room temperature. The reaction mixture is stirred for an additional one-half hour and then washed successively with a sodium bicarbonate solution, water and finally saturated sodium chloride solution. The organic solution is evaporated to afford the benzhydryl ester of 7-methoxy-3-methyl-7-(2-thienylacetamido)-2-cephem-4-carboxy-1-oxide.

EXAMPLE 12

Benzhydryl ester of 7-methoxy-3-(N-piperidinothiocarbonyl-thiomethyl)-7-(2-thienylacetamido)-2-cephem-4-carboxy-1-oxide Step A: Benzhydryl ester of 7-methoxy-3-(N-piperidinothiocarbonylthiomethyl)-7-(2-thienylacetamido)-2-cephem-4-carboxylic Acid A mixture of benzhydryl ester of 3-bromomethyl-7-methoxy-7-(2-thienylacetamido)-2-cephem-4-carboxylic acid (1.2 g.), toluene (50 ml.) and piperidine dithiocarbamate sodium salt (1.5 g.) is agitated with a high speed stirrer for five hours. The reaction mixture is filtered, the filtrate is concentrated and the product purified by chromatography on silica gel.

Step B: Benzhydryl ester of 7-methoxy-3-(N-piperidinothiocarbonylthiomethyl)-7-(2-thienylacetamido)-2-cephem-4-carboxy-1-oxide By following substantially the procedue described in Example 1, Step D, the product of Step A is oxidized to afford the benzhydryl ester of 7-methoxy-3-(N-piperidinothiocarbonylthiomethyl)-7-(2-thienylacetamido)-2-cephem-4-carboxy-1-oxide.

By substituting in Example 12, Step A, an equimolar quantity of 2-methyl-1,3,4-thiadiazol-5-thiol sodium salt for the piperidine dithiocarbonate sodium salt employed therein and following substantially the procedure described in Steps A and B of Example 12 there is obtained the benzhydryl ester of 7-methoxy-3-(2-methyl-1,3,4-thiadiazol-5-thiomethyl)-7-(2-thienylacetamido)-2-cephem-4-carboxy-1-oxide.

EXAMPLE 13

Benzhydryl ester of 7-methoxy-3-(N-pyridylmethyl)-7-(2-thienylacetamido)-2-cephem-4-carboxy-1-oxide bromide Step A: Benzhydryl ester of 7-methoxy-3-(N-pyridylmethyl)-7-(2-thienylacetamido)-2-cephem-4-carboxylic acid bromide To a solution of the benzhydryl ester of 3-bromomethyl-7-methoxy-7-(2-thienylacetamido)-2-cephem-4-carboxylic acid (1.0 g.) in benzene (10 ml.) is added pyridine (1.0 ml.). The reaction mixture is kept overnight at room temperature. The benzene and excess pyridine are removed under reduced pressure to afford the desired product.

Step B: Benzhydryl ester of 7-methoxy-3-(N-pyridylmethyl)-7-(2-thienylacetamido)-2-cephem-4-carboxy-1-oxide bromide The product of Step A is oxidized in substantially the same manner as described in Example 1, Step D, to afford the benzhydryl ester of 7-methoxy-3-(N-pyridylmethyl)-7-(2-thienylacetamido)-2-cephem-4-carboxy-1-oxide bromide.

EXAMPLE 14

Benzhydryl ester of 3-carbamoyloxymethyl-7-methoxy-7-(2-thienylacetamido)-2-cephem-4-carboxy-1-oxide Step A: Benzhydryl ester of 3-carbamoyloxymethyl-7-methoxy-7-(2-thienylacetamido)-2-cephem-4-carboxylic Acid To calcium carbamate (25 g.) in dimethylformamide (100 ml.) is added a solution of the benzhydryl ester of 3-bromomethyl-7-methoxy-7-(2-thienylacetamido)-2-cephem-4-carboxylic acid (5.0 g.) in dimethylformamide (20 ml.). The reaction mixture is stirred at room temperature overnight. The reaction mixture is diluted with water and the product is extracted with methylene chloride. The methylene chloride solution is washed with an aqueous sodium bicarbonate solution and then with water. The solution is then dried over magnesium sulfate, filtered and the solvent removed to afford the benzhydryl ester of 3-carbamoyloxymethyl-7-methoxy-7-(2-thienylacetamido)-2-cephem-4-carboxylic acid.

Step B: Benzhydryl ester of 3-carbamoyloxymethyl-7-methoxy-7-(2-thienylacetamido)-2-cephem-4-carboxy-1-oxide By following substantially the procedure as described in Example 1, Step D, the product of Step A is oxidized to afford the benzhydryl ester of 3-carbamoyloxymethyl-7-methoxy-7-(2-thienylacetamido)-2-cephem-4-carboxy-1-oxide.

Preparation of Starting Materials

7-Methoxy-3-methoxymethyl-7-(2-thienylacetamido)-3-cephem-4-carboxylic Acid

Step A: Monosodium Salt of 7β-(D-5-amino-5-carboxyvaleramido)-3-carbamoyloxymethyl-7-methoxy-3-cephem-4-carboxylic Acid Modified Fermentation Process:

Step 1: slants

A lyophilized tube of streptomyces lactamdurans culture (MA-2908; NRRL-3802) was opened asceptically and the organism transferred to a medium of the following composition:

Medium XI:
1% Blackstrap Molasses
1% National Brewer's Yeast
2.5% Difco agar pH 7.0
Water to volume The slants are inoculated for seven days at 28°C. When stored in the cold, the slants are stable for more than 13 weeks.

Step 2: Seed Stages: Two Stage System

First Seed: The first seed is inoculated directly from the slant of Step 1 to 40 ml. of 1% Primary Dried Yeast N.F., pH 7.0 (obtained from the Yeast Product Corporation) in a 250 ml. baffled Erlenmeyer flask. The flasks were then shaken on a 220 rpm. rotary shaker with a 2 inch throw at 28°C. for a period of from two to three days.

Second Seed: A 2.5% inoculum from the first seed stage was added to a flask containing a 2% Fleischmann S-150 yeast autolysate, pH 7.0. The growth in this stage is characteristically light and the incubation, performed as in the first stage, was not extended beyond 48 hours.

Step 3: Production Medium

The production medium contains per liter of distilled water: 30 g. distiller's solubles: 7.5 g. of Primary Dried Yeast N.F. and 0.25% v/v Mobilpar-S defoamer. The medium is adjusted to pH 7.0 with a small amount of concentrated sodium hydroxide solution, dispensed into Erlenmeyer flasks and autoclaved for 15 or 20 minutes at 121°C. After cooling the medium received a 2.5% inoculum of the seed obtained in Step 2. The time of incubation can vary from about 50 hours to 100 hours but an incubation period of about 72 hours is preferred. The volume of media in each flask can vary from 30 to 50 ml. but 40 ml. was used routinely. The level of inoculum can vary from 1% to 5%; but, in practice, a 2.5% level is generally employed.

Step 4: Assay

When the fermentation was complete, the cells were removed by centrifugation and the broth was diluted with phosphate buffer, pH 7.0. The concentration of 7β-(D-5-amino-5-carboxyvaleramido)-3-(carbamoyloxymethyl)-7-methoxy-3-cephem-4-carboxylic acid in the fermentation broth was determined by the standard biological-disc assay method. The assay organism employed was Vibrio percolans (ATCC 8461). Filter paper discs are emersed into the diluted broths and placed on the surface of agar-containing Petri dishes that had been inoculated with the assay organism Vibrio percolans (ATCC 8461). Also placed on these Petri dishes are discs that had been dipped previously in standard solutions containing known concentrations of 7β-(D-5-amino-5-carboxyvaleramido)-3-carbamoyloxymethyl)-7-methoxy-3-cephem-4-carboxylic acid. The discs were incubated overnight at 28° C. and the diameters of the zones of inhibition recorded. The concentration of product and the fermented broth is calculated by interpolation from the standard curve which relates zone diameter with the known concentrations of standard solutions of the product. By this procedure it was calculated that Sreptomyces lactamdurans MS-2908 produced 78.6 μg./ml. of 7β-(D-5-amino-5-carboxyvaleramido)-3-carbamoyloxymethyl-7-methoxy-3-cephem-4-carboxylic acid in the modified fermentation process.

Step 5: Isolation

The filtered broth is adjusted to pH 7.0 with dilute hydrochloric acid and 2900 ml. is passed through a column containing a strongly basic anion exchange resin (100 g.) having a styrene-divinylbenzene matrix (Dowex 1 × 2 chloride cycle resin) at 10 ml./minute. The spent solvent is collected in 500 ml. fractions. The resin column is washed with water and eluted with 3% ammonium chloride in 90% methanol. The eluate is collected in 100 ml. fractions. The spent fractions are combined, the pH adjusted to pH 7.2 to 8.0 with dilute sodium hydroxide and adsorbed on a strongly basic anion exchange resin (100 g.) having a styrene-divinylbenzene matrix (Dowex 1 × 2 chloride cycle resin) at 14 ml./minute. The column is washed with water and eluted with 5% aqueous sodium chloride. The eluate is collected in 50 ml. fractions and concentrated. The concentrate is diluted with 500 ml., adjusted from pH 8.8 to pH 2.0 with dilute hydrochloric acid and adsorbed on 25 ml. of a strongly acidic cation exchange resin of the sulfonate type having a styrene-divinylbenzene matrix (Dowex 50 × 2 hydrogen cycle resin) at 2.5 ml./minute. The column is washed with 25 ml. of water then eluted with 2% pyridine until the pH of the column effluent rose to pH 7 (54 ml.). The eluate thus obtained is adjusted to pH 8.0 with dilute sodium hydroxide and concentrated under vacuum to remove the pyridine and afford the monosodium salt of 7β-(D-5-amino-5-carboxyvaleramido)-3-carbamoyloxymethyl-7-methoxy-3-cephem-4-carboxylic acid.

Elemental analysis for $C_{16}H_{21}N_4SO_9Na$:

Calc.: C, 41.0%; H, 4.5%; N, 12.0%; S, 6.8%;
Found: C, 39.31%; H, 4.76%; N, 11.16%; S, 6.46%.

Step B: 7-(D-5-trichloroethoxycarbonylamino-5-carboxyvaleramido)-3-carbamoyloxymethyl-7-methoxy-3-cephem-4-carboxylic Acid The monosodium salt of 7-(D-5-amino-5-carboxyvaleramido)-3-carbamoyloxymethyl-7-methoxy-3-cephem-4-carboxylic acid (20.5 gm.) is dissolved in a mixture of acetone (80 ml.) and aqueous 10% dipotassium hydrogen phosphate (240 ml.). To this solution is added dropwise trichloroethoxycarbonyl chloride (25 gm., 118 mmoles) in acetone (80 ml.). During the addition the pH of the solution is kept at 9.1 by gradual addition of 2.5 N sodium hydroxide solution. After 30 minutes the mixture is extracted with ethyl acetate, the ethyl acetate layer discarded, and the aqueous layer is acidified to pH 2.5 with concentrated hydrochloric acid. The precipitated product is extracted into ethyl acetate. After drying over sodium sulfate and removing the solvent under vacuum the title compound is obtained as an oil. This crude product is used without purification in the next step.

Step C: Di-benzyhydryl ester of 7-(D-5-trichloroethoxycarbonylamino-5-carboxyvaleramido)-3-carbamoyloxymethyl-7-methoxy-3-cephem-4-carboxylic Acid To a solution of 7-(D-5-trichloroethoxycarbonylamino-5-carboxyvaleramido)-3-carbamoyloxymethyl-7-methoxy-3-cephem-4-carboxylic acid in ethyl acetate (500 ml.) is added diphenyldiazomethane (17 gm.) in ether (200 ml.). After agitating the mixture overnight, it is extracted successively with sodium bicarbonate and sodium chloride solutions. The solvent is evaporated from the dried solution to afford a crude product which is purified by chromatography on silica gel. A 2:1 mixture of chloroform and ethyl acetate is used for elution. This material showed a single spot of thin layer chromatography.

UV: λmax. 2650 γ7000 (CH$_3$OH)

Step D: Dibenzhydryl ester of 7[(D-5-trichloroethoxycarbonylamino-5-carboxyvaleryl)-β-thienylacetyl)-amino]-3-carbamoyloxymethyl-7-methoxy-3-cephem-4-carboxylic Acid A mixture of dibenzhydryl ester of 7-(D-5-trichloroethoxycarbonylamino-5-carboxyvaleramido)-3-carbamoyloxymethyl-7-methoxy-3-cephem-4-carboxylic acid (6.0 gm., 6.3 mmoles), N-trimethylsilyl trifluoroacetamide (4.7 gm., 40 mmoles), 2-thienylacetyl chloride (3.42 ml., 25 mmoles), and chloroform (50 ml.) is warmed at 47° C. for 16 hours. After the solvent is removed by evaporation, the crude reaction mixture is extracted with hexane and further purified by chromatography on 1 kg. of silica gel using 10% ethylacetate in chloroform as the eluant. The purified product exhibits a satisfactory NMR spectrum.

UV: λmax: 265 ε5810 (CH$_3$OH) and shows a single spot on thin layer chromatography Step E: Benzhydryl ester of 3-carbamoyloxymethyl-7-methoxy-7-(2-thienylacetamido)-3-cephem-4-carboxylic Acid The dibenzyhydryl ester of 7-[(D-5-trichloroethoxycarbonylamino-5-carboxyvaleryl)-(2-thienylacetyl-)amino]-3-carbamoyloxymethyl-7-methoxy-3-cephem-4-carboxylic acid (4.2 gm., 3.8 mmoles) is dissolved in ethyl acetate (30 ml.) and added to a mixture of 90% aqueous acetic acid (30 ml.) and zinc dust (12 gm.). The mixture is stirred vigorously for 5½ hours at room temperature. After the zinc is filtered off, the excess acetic acid is removed by washing the ethylacetate solution with water. The title compound is isolated in the same manner as described above in Step D. It is characterized by thin layer chromatography (7% CH$_3$OH in 1:1 CHCl$_3$:n-hexane) as a single spot material.

IR: (CHCl$_3$) 1740, 1800 cm$^{-1}$;
UV: λmax. 263 ε5800

The term "Florisil" used in the application is the tradename for an activated magnesium silicate.

By following substantially the procedures described in Examples 1 and 4, all of the products disclosed herein may be prepared by the novel process of this invention. Thus, by substituting the appropriate hydrohalic acid for the hydrogen bromide of Example 1, Step B, or by substituting for phenol of Example 4, Step A, an appropriate compound containing an active hydrogen and following the respective procedure described in Example 1, Steps A-D and Example 4, Steps A and B, all of the products described in Table I may be prepared.

The following equation, together with Table I, illustrates the starting materials and the intermediates and products which may be prepared.

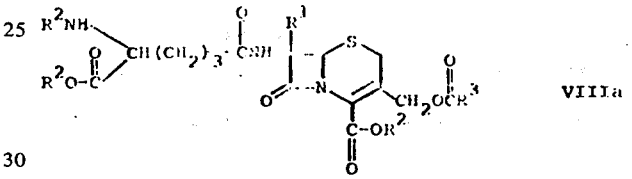

VIIIa

↓ Acylating Agent / Silyl Compound

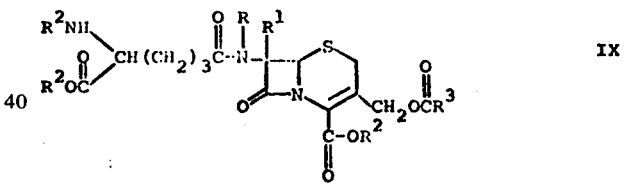

IX

↓ Removal of Protecting Group and Cleavage of Aminoadipoyl Side Chain

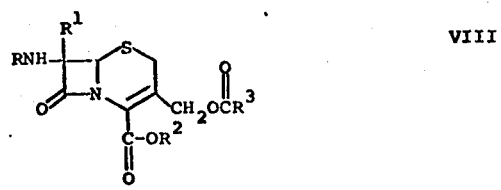

VIII

↓ Isomerizing Agent

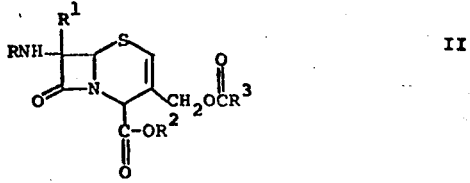

II

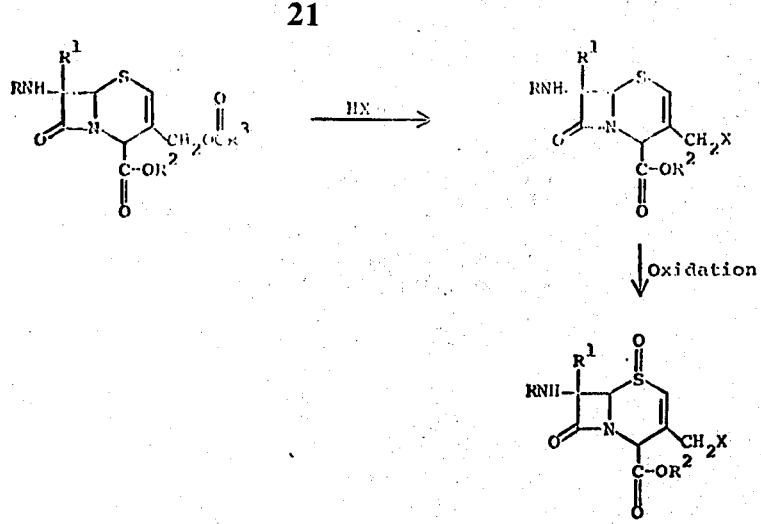

TABLE I

| Ex. No. | R | R¹ | R² | R³ | X |
|---|---|---|---|---|---|
| 15 | phenyl-CH(NH₂)-C(=O)- | $-OCH_3$ | $-CCl_3$ | $-NH_2$ | Cl |
| 16 | 2-thienyl-CH₂-C(=O)- | $-OCH_3$ |  $-CH_2$-phenyl | $-NH_2$ | 2,4-dihydroxyphenyl |
| 17 | 2-furyl-CH₂-C(=O)- | $-OCH_3$ | $-CH_2$-(3,5-dimethoxyphenyl) | $-NH_2$ | $-OC(=O)(CH_2)_2CH_3$ |
| 18 | phenyl-CH(NH₂)-C(=O)- | $-OCH_3$ | $-CH(\phi)_2$ | $-NH_2$ | $-CH(C(=O)CH_3)(C(=O)OCH_3)$ |
| 19 | 2-thienyl-CH₂-C(=O)- | $-OCH_3$ | $-CH(\phi)_2$ | $-NH_2$ | $-O-C(=O)$-phenyl |
| 20 | 2-thienyl-CH₂-C(=O)- | $-OCH_3$ | $-CH_2OCH_3$ | $-NH_2$ | $-CCF_3$ (with =O) |
| 21 | phenyl-CH₂-C(=O)- | $-OCH_3$ | $-CH(\phi)_2$ | $-NH_2$ | I |
| 22 | phenyl-CH(NH₂)-C(=O)- | $-OCH_3$ | $-CH(\phi)_2$ | $-CH_3$ | Br |

The examples are illustrative of the novel method disclosed, however, it is to be understood that the invention is not limited by the specific examples but embraces all the variations and modifications falling within the scope of the foregoing discussion and appended claims.

What is claimed is:
1. A compound of the formula:

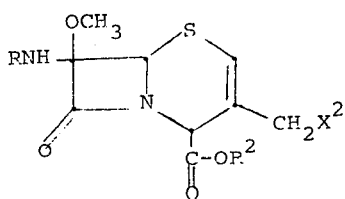

wherein R is an acyl radical of the formula:

wherein $R^6$ is benzyl, p-hydroxybenzyl, α-aminobenzyl, α-carboxybenzyl, α-azidobenzyl, allylthiomethyl, butylmercaptomethyl, D(or L)-4-amino-4-carboxybutyl, α-chlorocrotylmercaptomethyl, phenoxymethyl, 2-pentenyl, n-amyl, n-heptyl, ethyl, 3- or 4-nitrobenzyl, phenethyl, β,β-diphenethyl, thienyl, phenylthiomethyl, 2-thienyl, α-amino-2-thienylmethyl, α-methylaminobenzyl, α-(N-methylsulfamino)benzyl, D(—)-α-guanidino-2-thienylmethyl, D(—)-α-guanidinobenzyl, 4-guanidinophenoxymethyl, 4-guanidinomethylbenzyl, cyanomethyl, 2,6-dimethoxy-4-guanidinophenyl, 2- or 3-furylmethyl and 1-H-tetrazol-1-ylmethyl;

$R^2$ is a protecting group selected from trichloroethyl, tertbutyl, benzoylmethyl, p-methoxybenzyl, benzyl, benzhydryl or methoxymethyl or hydrogen; and $X^2$ is halo selected from the group consisting of chlorine, bromine and iodine; cyano or lower alkoxy.

2. A compound according to claim 1 wherein R is α-aminoadipoyl, α-aminophenylacetyl or 2-thienylacetyl; $X^2$ is halo selected from the group consisting of chlorine, bromine or iodine; and $R^2$ is hydrogen or a protecting group selected from trichloroethyl, tert-butyl, benzoylmethyl, p-methoxybenzyl, benzyl, benzhydryl or methoxymethyl.

3. A compound of the formula:

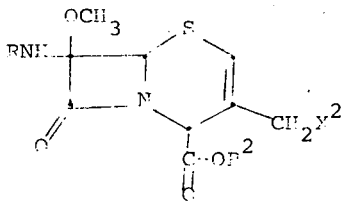

wherein R is an acyl radical of the formula

wherein
$R^6$ is α-aminobenzyl;
$X^2$ is bromo; and
$R^2$ is hydrogen, trichloroethyl, tert-butyl, p-methoxybenzyl, benzhydryl or methoxymethyl.

4. A compound of the formula:

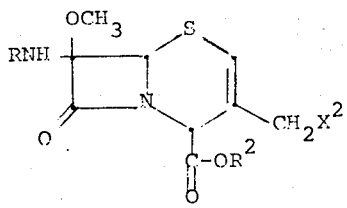

wherein R is 2-thienylacetyl;
$X^2$ is bromo; and
$R^2$ is hydrogen, trichloroethyl, tert-butyl, p-methoxybenzyl, benzhydryl or methoxymethyl.

5. A compound of the formula:

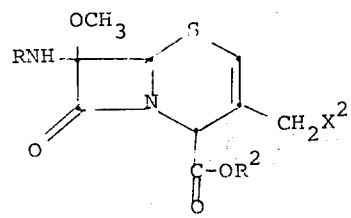

wherein R is α-aminoadipoyl;
$X^2$ is bromo; and
$R^2$ is hydrogen, trichloroethyl, tert-butyl, p-methoxybenzyl, benzhydryl or methoxymethyl.

6. The benzhydryl ester of 3-bromomethyl-7-methoxy-7-(2-thienylacetamido)-2-cephem-4-carboxylic acid.

* * * * *